United States Patent [19] [11] Patent Number: 4,863,874
Wassef et al. [45] Date of Patent: Sep. 5, 1989

[54] METHOD FOR DETECTING PHOSPHATIDYLINOSITOL THROUGH BINDING TO CONCANAVALIN A

[75] Inventors: Nabila M. Wassef, Potomac, Md.; Carl R. Alving, Washington, D.C.

[73] Assignee: The United States of America as represented by the Secretary of the Army, Washington, D.C.

[21] Appl. No.: 884,691

[22] Filed: Jul. 11, 1986

[51] Int. Cl.$^4$ .............................................. G01N 33/53
[52] U.S. Cl. .................................... 436/501; 436/71; 436/104; 436/131
[58] Field of Search ................ 436/71, 103, 104, 131, 436/501

[56] References Cited

PUBLICATIONS

Wassef et al., Biochem. Biophys. Res. Commun., vol. 130, No. 1, pp. 76–83, Jul. 16, 1985.
Dean et al., Biochim. Biophys. Acta, vol. 322, pp. 141–144, 1973.
Kozloff et al., Science, vol. 226, No. 4676, pp. 845–846, 1984.
Hardman et al., Nature New Biology, vol. 237, pp. 54–55, 1972.
Lis et al., Ann. Rev. Biochem., vol. 42, pp. 541–547, 1973.
Goldstein et al., Biochemistry, vol. 4, No. 5, pp. 876–883, 1965.
Read et al., Biochim. Biophys. Acta, vol. 470, pp. 325–330, 1977.
Suzuki et al., J. Biochem., vol. 94, pp. 373–377, 1983.
Nicholson, G. L. (1974), Int. Rev. Cytol., vol. 39, pp. 89–190.
Goldstein, I. J. and Hayes, C. E. (1978), Advan. Carbohyd. Chem. Biochem., vol. 35, pp. 127–340.
Surolia, A., Bachhawat, B. K., and Podder, S. K. (1975), Nature, vol. 257, pp. 802–804.
Redwood, W. R., and Polefka, T. G. (1976), Biochim. Biophys. Acta., vol. 455, pp. 631–643.
Boldt, D. H., Speckart, S. F., Richards, R. L., and Alving, C. R. (1977), Biochem. Biophys. Res. Comm., vol. 74, pp. 208–214.
Maget-Dana, R., Roche, A., and Monsigny, M. (1977), FEBS Lett., vol. 79, pp. 305–309.
Curatolo, W., Yau, A. O., Small, D. M., and Sears, B. (1978), Biochemistry, vol. 17, pp. 5740–5744.
Williams, T., Pleassas, N. R., and Goldstein, I. J. (1979), Arch. Biochem. Biophys., vol. 195, pp. 145–151.
Orr, G. A., Rando, R. R., and Bangerter, F. W. (1979), J. Biol. Chem., vol. 254, pp. 4721–4725.
Slama, J. S., and Rando, R. R. (1980), Biochemistry, vol. 19, pp. 4595–4600.
Ghosh, P., Bachhawat, B. K., and Surolia, A. (1981), Arch. Biochem. Biophys., vol. 206, pp. 454–457.
Mansson, J., and Olofsson, S. (1983), FEBS Lett., vol. 156, pp. 249–252.

*Primary Examiner*—Robert J. Hill, Jr.
*Attorney, Agent, or Firm*—Werten F. W. Bellamy; Anthony T. Lane

[57] ABSTRACT

A method for the specific detection of inositol and phosphatidylinositol within a model membrane such as liposomes or within a cellular system such as T lymphocytes.

1 Claim, 2 Drawing Sheets

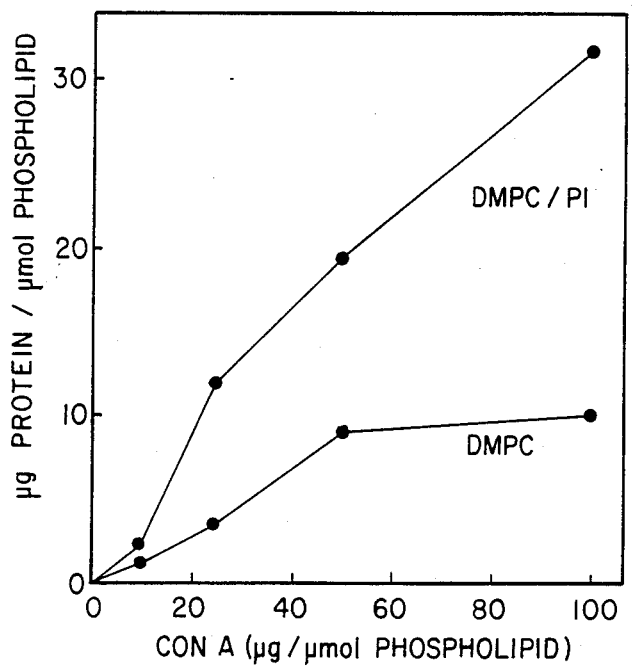
FIG. 1
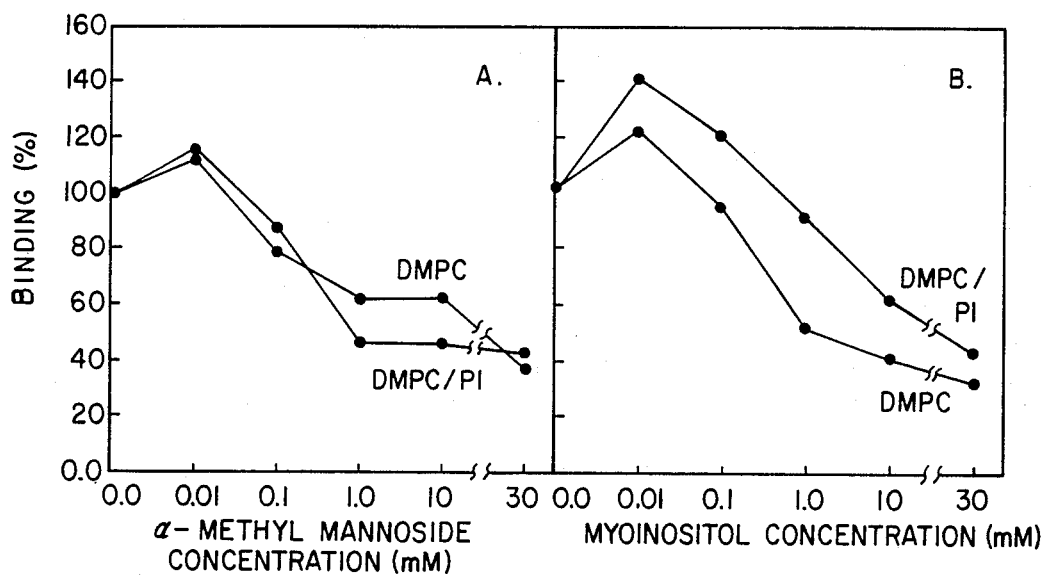
FIG. 2a
FIG. 2b

METHOD FOR DETECTING PHOSPHATIDYLINOSITOL THROUGH BINDING TO CONCANAVALIN A

BACKGROUND OF THE INVENTION

1. Field of the Invention

This invention relates to a method for the specific detection of phosphatidylinositol within a model membrane such as liposomes or a cellular system such as T lymphocytes.

2. Prior Disclosure

The following abbreviations used in this application are intended to have the following meaning: Con A (concanavalin A); PL (phospholipid); DMPC (dimyristoyl phosphatidylcholine); PI (phosphatidylinositol); α-MM (α-methyl mannoside); HBS (Hank's balanced salt solution); and MEM (minimum essential medium).

All publications or patents mentioned in this specification are herein incorporated by reference.

Applicants reported in *Biochemical and Biophysical Research Communications*, Vol. 74, page 208 (1977) that Con A could bind specifically to liposomes containing phospholipids but lacking glycoconjugates. Lectins, such as Con A, have been used extensively to probe mammlian cell structures and to study lymphocyte mitogenesis and numerous other cell functions. Generally, it has been believed by the scientific community that Con A binds to mannose (or glucose) which are the specific receptors for Con A on the cell surface.

SUMMARY OF THE INVENTION

This invention is directed to a method for detecting, separating, or purifying PI. Plant lectins (i.e. Con A) bind to sugars and are known to be useful in identifying and locating sugar molecules (i.e. purifying glycoproteins). Surprisingly, this invention relates to the discovery that Con A can be used to bind to inositol or PI which are not sugars. The PI serves as a receptor for Con A. This receptor activity is in addition to that ordinarily attributed to binding sugars such as mannose or glucose. Sugars (carbohydrates) contain the functional groups (carboxy (C(O)OH) or aldehyde (C(O)H)), whereas PI is characterized by the presence of inositol, a compound containing cyclitol groups (i.e. a ring structure with hydroxy substituents).

Prior to this discovery, it was not recognized that Con A binds to PI. Therefore, all binding of Con A was presumed to be attributable to its binding to sugar (carbohydrate) molecules. Hence, this invention is especially useful as (1) a method for purifying proteins that have PI attached and (2) a probe to identify the site of action of PI in the cell. Applicants have discovered that the binding of Con A to the liposomes was greatly increased (up to 5 fold) by the presence of PI in the liposomes. Furthermore, the binding of Con A to PI-liposomes was specific and could be inhibited by either α-methyl mannoside or by myo-inositol. It was also found that Con A-induced lymphocyte mitogenesis could be inhibited either by α-methyl mannoside or by myo-inositol. Simultaneous addition of both inhibitors to Con A and liposomes showed that inhibition was non-competitive: α-methyl mannoside was more inhibitory to liposomes lacking PI, and myo-inositol was more inhibitory to liposomes containing PI. This suggests that the binding site for inositol might be different than that for mannose. Equilibrium dialysis and Scatchard plots revealed four (4) binding sites each for inositol and mannose at neutral pH. The binding constants of Con A were $0.13 \times 10^4$ and $0.25 \times 10^4$ liters/mole respectively for inositol and mannose. In conclusion, Con A binds specifically to the inositol portion of PI.

Lectins are proteins that are characterized by the property of having binding sites for sugars. Numerous glycoconjugates, including glycoproteins (Nicolson, G. L. (1974) *Int. Rev. Cytol.*, Vol. 39, pages 89–190; Goldstein, I. J., and Hayes, C. E. (1978) *Advan. Carbohyd. Chem. Biochem.*, Vol. 35, pages 127–340; Roth, J. (1978) *Exp. Pathol.*, Vol. 16 (Suppl. 3), page 186) and glycolipids (Surolia, A., Bachhawat, B. K., and Podder, S. K. (1975) *Nature*, Vol. 257, pages 802–804; Redwood, W. R., and Polefka, T. G. (1976) *Biochim. Biophys. Acta.*, Vol. 455, pages 631–643; Boldt, D. H., Speckart, S. F., Richards, R. L., and Alving, C. R. (1977) *Biochem. Biophys. Res. Comm.*, Vol. 74, pages 208–214; Read, B. D., Demel, R. A., Wiegandt, H., and van Deenen, L. L. M. (1977) *Biochim. Biophys. Acts.*, Vol. 470, pages 325–330; Maget-Dana, R., Roche, A., and Monsigny, M. (1977) *FEBS Lett.*, Vol. 79, pages 305–309; Curatolo, W., Yau, A. O., Small, D. M., and Sears, B. (1978) *Biochemistry*, Vol. 17, pages 5740–5744; Williams, T., Pleassas, N. R., and Goldstein, I. J. (1979) *Arch. Biochem. Biophys.*, Vol. 195, pages 145–151; Orr, G. A., Rando, R. R., and Bangerter, F. W. (1979) *J. Biol. Chem.*, Vol. 254, pages 4721–4725; Slama, J. S., and Rando, R. R. (1980) *Biochemistry*, Vol. 19, pages 4595–4600; Ghosh, P., Bachhawat, B. K., and Surolia, A. (1981) *Arch. Biochem. Biophys.*, Vol. 206, pages 454–457; Tamiko, S., Inoue, K., Nojima, S., and Wiegandt, H. (1983) *J. Biochem.*, Vol. 94, pages 373–377; Mansson, J., and Olofsson, S. (1983) *FEBS Lett.*, Vol. 156, pages 249–252; Smith, D. F. (1983) *Biochem. Biophys. Res. Comm.*, Vol. 115, pages 360–367) can be bound by lectins. Plant lectins have been used extensively to probe mammalian membrane structures and to study lymphocyte mitogenesis and a variety of other membrane functions (reviewed by Sharon, N., and Lis, H. (1975) in *Methods in Membrane Biology* (E. D. Korn, edition), pages 147–200, Plenum Press, NY). Although plant lectins do interact with cells by binding to specific saccharides on the cell surface, several carbohydrate-free liposomes and lipid membranes can also bind to lectins (Boldt, D. H., Speckart, S. F., Richards, R. L., and Alving, C. R. (1977) *Biochem. Biophys. Res. Comm.*, Vol. 74, pages 208–214; Read, B. D., Demel, R. A., Wiegandt, H., and van Deenen, L. L. M. (1977) *Biochim. Biophys. Acta.*, Vol. 470, pages 325–330; van der Bosch, J., and McConnell, H. M. (1975) *Proc. Nat. Acad. Sci. USA*, Vol. 72, pages 4409–4413). In illustrating the operability of the present invention, we demonstrate specific binding of Con A to PI in liposomes and inhibition of such binding by either myo-inositol or α-methyl mannoside. We also demonstrate that these inhibitors are capable of suppressing the mitogenic response in murine lymphocytes to Con A.

BRIEF DESCRIPTION OF THE DRAWINGS

A more complete appreciation of the invention and many of the attendant advantages thereof will be readily obtained by reference to the following DETAILED DESCRIPTION OF THE INVENTION when considered in conjunction with the accompanying drawings, wherein:

FIG. 1 shows Con A binding to liposomes. One hundred (100) μl of liposomes containing DMPC/Cholesterol in a 2:1.5 molar ratio, or DMPC/PI/Cholesterol in a 1:1:1.5 molar ratio, were incubated with Con A in the concentrations indicated for 45 minutes at 25° C., in a final volume of 1 ml bicarbonate-saline buffer. After incubation, the liposomes were washed twice with 2 ml portions of bicarbonate-saline and specific lectin binding to liposomes was determined. Controls without liposomes were substracted from each result to compensate for slight non-specific binding to the glass tubes.

FIGS. 2a and 2b show the inhibition of Con A binding to liposomes by α-methyl mannoside or myo-inositol. Similar incubations as those described in FIG. 1 were set up with liposomes and Con A. α-MM (FIG. 2a) or myo-inositol (FIG. 2b) were used as inhibitors in the concentrations indicated.

DETAILED DESCRIPTION OF THE INVENTION

Figure 3:
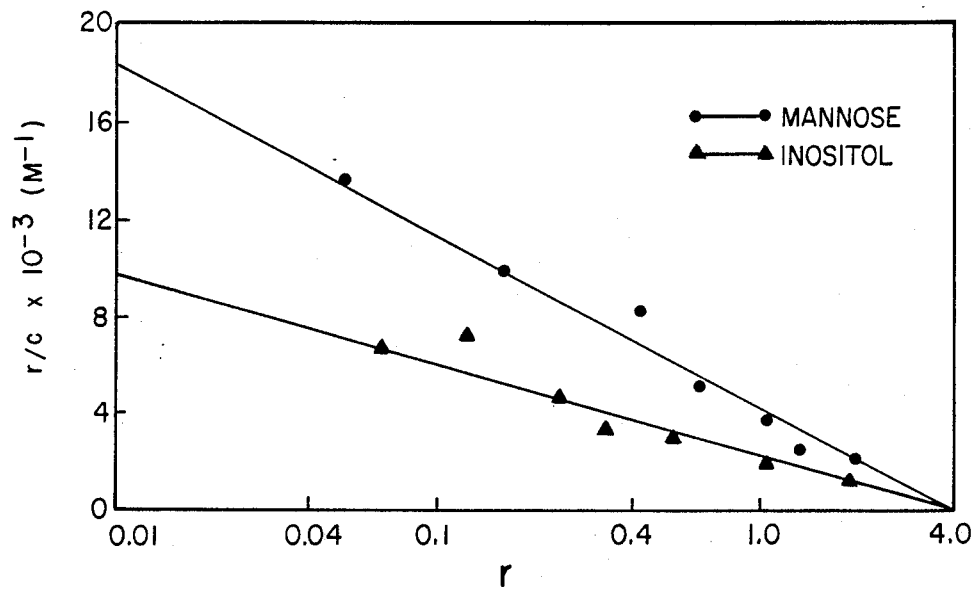
FIG. 3 shows the equilibrium dialysis data for the binding of -MM and myo-inositol to Con A plotted by the method of Scatchard.
Figure 4:
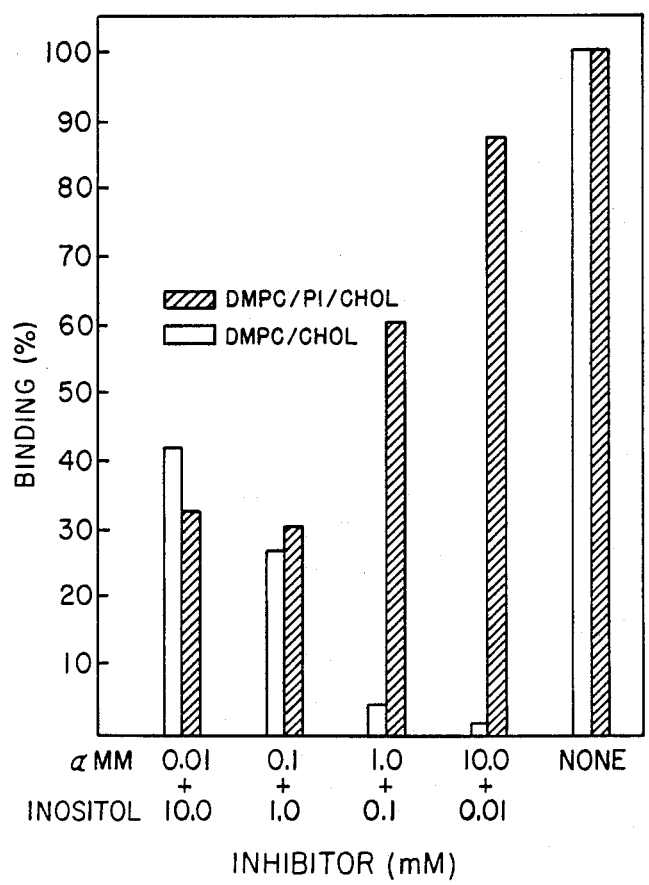
FIG. 4 shows the inhibition of Con A binding to liposomes by mixtures of α-MM and myo-inositol. Similar incubations as those described in FIG. 1 were set up with liposomes and Con A. Myo-inositol and α-MM were mixed together as inhibitors in the concentrations indicated.

Our novel method is useful in the detection of liposomes containing phosphatidylinositol. Using liposomes composed of dimyristoyl phosphatidylcholine (DMPC), phosphatidylinositol (PI) and cholesterol (Chol), we were able to demonstrate a significant binding of Con A to these phospholipid membranes. Unexpectedly, Con A binding was greatly enhanced when the liposomes contained PI compared to liposomes lacking PI (FIG. 1). We then started to characterize this binding and to our surprise it proved specific and was inhibited by α-methyl mannoside (FIG. 2a) as well as by myo-inositol, a component of the PI molecule (FIG. 2b). Moreover, further studies showed that the binding constants for mannose and inositol were not widely different and that the Con A molecule at neutral pH possesses 4 binding sites each for inositol and mannose (FIG. 3). However, the binding sites for inositol seem to be different and distinct from those of mannose since by mixing both inhibitors we were unable to obtain an additive inhibition. Inositol was more inhibitory to Con A binding to liposomes containing PI while α-methyl mannoside was more inhibitory to liposomes lacking PI (FIG. 4).

Most of the research published to date proceeded under the presumption that Con A binds to mannose (or glucose) and all of the effects of Con A, activation of lymphocytes for example, are due to this binding. We proved that Con A also binds to inositol and PI and that certain effects elicited by Con A could be due to Con A binding to PI specifically. As an example, we demonstrated that Con A-induced mitogenesis of T lymphocytes was inhibited by inositol and that Con A was presumably binding to PI. This opens a potential new avenue for interpreting Con A cellular effects. Also by using liposomes to show Con A binding to PI, we have a defined model system easy to reproduce and to extrapolate from. The invention is the use of Con A to bind to inositol or PI and the invention, as a further step, includes the use of such binding on membrane surfaces for the purpose of affecting cell functions. The binding of Con A to inositol or PI could be used in cell-free systems to identify or help to purify inositol (or PI)-conjugated lipids or proteins. The binding could also be used to influence some or all of the myriad cellular, hormonal, oncological, neurological, etc. functions that have been associated with ranges of PI metabolism as described in Michell, R. H. (1975) *Biochim. Biophys Acta.*, Vol. 415, pages 81-147; Irvin, R. F., Dawson, R. M. C. and Freinkel, N. (1982) in *Contemporary Metabolism*, edition, Freinkel, N., (Plenum, NY), Vol. 2, pages 301-342; Farese, R. V. (1983) *Metabolism*, Vol. 32, pages 628-641; and Hokin, L. E. (1985) *Ann. Rev. Biochem.*, Vol. 54, pages 205-235.

By discovering a new receptor for Con A, namely PI, we have opened a potential new field of research which involves all the possible applications of Con A to study cellular and immunological properties of cells.

The discovery that Con A binds to PI or other inositol-containing-molecules can be widely used by medical researchers both in government and industry to investigate and modulate specific cellular response.

We have discovered a binding effect that is constant, reproducible and universal and we have defined it and characterized it. Furthermore, we have applied it to Con A-induced T lymphocyte mitogenesis and we have proved inhibition of mitogenesis by inositol. Two published reports have previously claimed that Con A might bind to PI or inositol (L. M. Kozloff, et al., *Science*, Vol. 226, pages 845-846 (1984) and K. D. Hardman, et al., *Nature New Biology*, Vol. 237, pages 54 and 59 (1972). The first report claiming that PI was a binding site for Con A was not a supportable or reasonable claim from the evidence presented by L. M. Kozloff, et al. First, the evidence is only indirect. PI was used to inhibit agglutination of red blood cells by Con A. There was no direct binding evidence that showed binding of Con A to PI on red blood cells or specific binding of Con A to free PI as a specific inhibitory mechanism. Second, nonspecific binding was not ruled out by testing other phospholipids related to PI. Third, the article is almost exclusively concerned with PI as a component of "ice-nucleating site" of certain bacteria, but direct chemical analysis failed to show the presence of PI in the bacterial cells. In the second article, by Hardman, et al., a tentative mathematical model of binding of myo-inositol to Con A was proposed in a system lacking membranes. This does not involve binding of Con A to PI or to inositol within a membrane or a cellular system as described in our invention. In contrast, we have demonstrated direct binding of Con A (by equilibrium dialysis—a widely accepted technique) to free inositol. The affinity of binding of Con A to inositol was measured by equilibrium dialysis and found to be similar to binding of mannose. Binding of Con A to PI was measured directly by simple protein analysis. Despite the statements made in the article, the data disclosed therein is not sufficient to enable one of ordinary skill in the area of science to which this invention relates to practice our invention.

Materials and Methods

Lipids were purchased from the following sources: DMPC and cholesterol from Calbiochem-Behring, La Jolla, CA; plant PI from Sigma Chemical Co., St. Louis, MO. Con A was purchased from Sigma. All inhibitors, including α-MM, myo-inositol, α-D-mannose, and α-L-fucose were from Sigma. Myo-[2-$^3$H]-inositol, 15.8 Ci/mmol, L-[6-$^3$H]-fucose, 16.8 Ci/mmol, D-[2-$^3$H]- mannose, 14.5 Ci/mmol, and [³H]-thymidine, 2.0 Ci/mmol were from New England Nuclear, Boston, MA.

Liposomes containing PL (DMPC, or DMPC/PI) and cholesterol in molar ratios 2/1.5 were used throughout. When PI was included in the liposomes, it was in a 1/1 molar ratio with DMPC. Preparation of liposomes (multilamellar vesicles) is reported in detail (Alving, C. R., Shichijo, S., and Mattsby-Baltzer, I. (1984) in *Liposome Technology*, (G. Gregoriadis, edition), Vol. II, pages 157–175, CRC, Boca Raton, FL). Briefly, lipids (PLs and cholesterol) were dried in vacuo in pear-shaped flasks and dispersed in a small volume of 0.15M NaCl with the aid of a few acid washed glass beads. The final PL concentration in the aqueous dispersion was 10 mM.

DESCRIPTION OF PREFERRED EMBODIMENT

Examples

The working examples set forth below illustrate, without any implied limitation, the use Con A to detect liposome containing PI.

Example 1

Studies on the binding of Con A to liposomes were performed as follows: Con A and inhibitors (if present) in the concentrations indicated in the individual figures were incubated with 100 μl of liposomes in a final volume of 1.0 ml of buffer for 45 minutes at 25° C. After incubation, liposomes were washed twice with 2 ml portions of 0.9% NaCl-0.01M NaHCO₃ (pH 7.0) and collected by centrifugation at 140,000 g for 5 minutes. Bicarbonate-saline was the buffer used throughout for solution, washing and dilutions. Specific protein binding to liposomes was measured by a Lowry assay adapted to measurement of proteins on liposomes as described previously (Alving, C. R., and Kinsky, S. C. (1971) *Immunochemistry*, Vol. 8, pages 325–343).

FIG. 1 demonstrated dose-dependent binding of Con A to DMPC and DMPC/PI liposomes. The binding of Con A to DMPC liposomes reached a saturation level of approximately 10 μg of protein/μmol of PL at an initial concentration of 50 μg of added Con A; however, binding of 100 μg of initially-added Con A to DMPC/PI liposomes was greatly increased compared to binding of 50 μg of initially-added Con A. Saturation of binding of Con A to the latter liposomes occurred only at levels above 100 μg of added Con A. Based on 3 experiments, total binding to DMPC/PI/CHOL reached a level of 42–50 μg of protein/μmol of PL when 200 μg of Con A was initially added (not shown). Therefore the presence of PI in the liposomes increased Con A binding by about 5 fold.

Con A binding to mannose is widely accepted as the major binding specificity for Con A, and inhibition of Con A by α-MM is often used as a criterion for specificity of binding (Lis, H. and Sharon, N. (1973) *Ann. Rev. Biochem.*, Vol. 42, pages 541–574). FIG. 2a shows that Con A binding to either DMPC or DMPC/PI liposomes was inhibited approximately 50% by a 1.0 mM concentration of α-MM. Although the binding of Con A was inhibited to the same extent for each type of liposome when expressed as percent of control, the absolute amounts of Con A binding, as shown in FIG. 1, were at least twice as high with DMPC/PI liposomes. Since Con A binding was increased by the presence of PI in the liposomes we tried to inhibit it by adding increasing concentrations of myo-inositol as a soluble inhibitor. FIG. 2b shows that myo-inositol did inhibit the binding of Con A to liposomal PLs, and although inhibition occurred in a pattern similar to that of α-MM the 50% level of inhibition was reached at a 10.0 mM concentration of myo-inositol. Furthermore, when a similar experiment was performed using increasing concentrations of α-L-fucose as an inhibitor of Con A binding to liposomes containing or lacking PI, no inhibition was observed. Therefore we conclude that the binding of Con A to PI is specific and probably involves the inositol moiety of PI.

In order to characterize further the binding of Con A to liposomal PLs, and especially to PI, we mixed varying concentrations of α-MM with varrying concentrations of myo-inositol. Our reasoning was that if α-MM and myo-inositol complete for the same binding site we would record similar inhibitions to those shown in FIG. 2. The results, in FIG. 4, demonstrate that inhibition of Con A binding to liposomes containing PI occurred when the concentrations of inositol were higher than those of a α-MM. The opposite occurred with liposomes lacking PI. These results suggested that myo-inositol and α-MM may have different binding sites on the Con A molecule.

Example 2

Equilibrium dialysis (microtechnique), as described by Karush, et al. (Karush, F., Karush, S. S. and Eisen, H. N. (1971) in *Methods of Immunology and Immunochemistry* (C. A. Williams, and M. W. Chase, Edition), Vol. III, pages 383–394, Academic Press, NY) was used to determine the binding of Con A to α-mannose, α-L-fucose, or myo-inositol. The data were plotted according to the method of Scatchard (Scatchard, G. (1949) *Ann. N.Y. Acad. Sci.*, Vol. 51, pages 660–672).

The binding of Con A to α-D-[³H]-mannose or myo-[³H]-inositol in 0.01M bicarbonate-saline, pH 7.0, at room temperature was investigated by equilibrium dialysis. The results are shown in FIG. 3 where r/c is plotted against r according to the method of Scatchard (Scatchard, G. (1949) *Ann. N.Y. Acad. Sci.*, Vol. 51, pages 660–672). The ratio of the molar concentration of the bound sugar to that of protein is represented by r, c is the molar concentration of free sugar, n is the number of binding sites and K, the binding constant. A molecular weight of 108,000 for Con A was used in the calculations since Con A is a tetramer at neutral pH and the monomer mol wt. is 27,000. Linear plots were obtained for both mannose and myo-inositol (FIG. 3) with values of n=4 which is in accordance with 1 binding site per monomer. When extrapolated to the r/c axis, binding constants of $0.13 \times 10^4$ 1/mole and $0.25 \times 10^4$ 1/mole were calculated for myo-inositol and D-mannose respectively. No binding could be detected for Con A with α-L-fucose under the same conditions.

Example 3

Mitogenic determination were made on 12 weeks old male C₃HeB/FeJ mouse (Jackson Laboratory, Bar Harbour, ME) spleen cells. The method used for cell preparation and assay of mitogenic activity is described elsewhere (Richardson, E. C., and Alving, C. R. (1984) *Rev. Infect. Dis.*, Vol. 6, pages 532–534). Briefly spleen cells were extracted into HSB (HEM Research Inc., Rockville, MD), purified on a Ficoll-Hypaque solution, washed twice with HBS and suspended in a medium containing Eagles MEM with Earle's salts (GIBCO, Grand Island, NY), penicillin 100 μg/ml and streptomycin 100 μg/ml (GIBCO), 5×10⁻⁵M 2-mercaptoethanol (Matheson, Coleman and Bell, Norwood, OH) and 5% fetal bovine serum (MBA, Walkersville, MD). Cultures containing $2 \times 10^5$ viable cells/0.2 ml were prepared in 96 wells microtiter plates (Linbro Chemical Co., New Haven, CT) containing Con A (6.0 g Con A protein/ml culture) with either 40 μmoles/ml α-MM or myo-inositol. Cultures were incubated at 37° C. in 5% $CO_2$ and air for 48 hours. Four hours prior to harvesting, the cells were pulsed with 1 μCi of [³H]-thymidine, harvested on glass fiber filters with a cell harvester and the radioactivity determined by liquid scintillation.

Since Con A has been used extensively as a tool to induce biological responses such as lymphocyte mitogenesis we decided to investigate if the binding of Con A to inositol would also supply to Con A-induced lymphocyte mitogenesis. Table 1 shows that either α-MM or myo-inositol when added simultaneously with Con A suppressed Con A-mediated mitogenesis of murine lymphocytes. α-MM was a more effective inhibitor than myo-inositol, but significant inhibition was observed with either compound (Table 1). No inhibition of Con A-induced lymphocyte mitogenesis was detected with α-L-fucose (not shown).

Conclusion

Binding of Con A to liposomes lacking glycoconjugates has been reported by several laboratories (Boldt, D. H., Speckart, S. F., Richards, R. L., and Alving, C. R. (1977) Biochem. Biophys. Res. Comm., Vol. 74, pages 208-214; Read, B. D., Damel, R. A., Wiegandt, H., and van Deene, L. L. M. (1977) Biochim. Biophys. Acta., Vol. 470, pages 325-330; van der Bosch, J., and McConnell, H. M. (1975) Proc. Nat. Acad. Sci. USA, Vol. 72, pages 4409-4413). We have shown that Con A binds much more to liposomes containing PI than to liposomes lacking PI (FIG. 1).

Binding to Con A to liposomes was "specific", based on the criterion that Con A binding inhibited by mannose is specific Goldstein, I. J., Hollerman, C. E., and Smith, E. E. (1965) Biochemistry, Vol. 4, pages 876-883; Reeke, G. N., Jr., Becker, J. W., Cunningham, B. A., Gunther, G. R., Wang, J. L., and Edelman, G. M. (1974) Ann. N.Y. Acad. Sci., Vol. 234, pages 369-382). Inhibition studies showed that Con A binding to liposomes either lacking or containing PI was inhibited by either α-MM (FIG. 2a) or by myo-inositol, a component of the PI molecule (FIG. 2b). This finding coupled with the ability of myo-inositol to inhibit a biological activity of Con A, lymphocyte mitogenesis, reveals a new role for membrane-bound inositol as well as a new and generally unrecognized specificity for Con A.

The above observations suggested the possibility that myo-inositol and mannose-containing glycoconjugates each could serve as Con A receptors and that they might compete for the same binding site on the Con A molecule. However, when myo-inositol and α-MM were simultaneously used as inhibitors an unexpected inhibition pattern was observed. When PI was present in the liposomes, myo-inositol was the more potent inhibitor and high concentrations of α-MM could not provide similar inhibition; in contrast, when PI was absent from liposomes α-MM was a more potent inhibitor than inositol (FIG. 4). These results suggested that myo-inositol and mannose may have different binding sites. Equilibrium dialysis experiments demonstrated that both mannose and myo-inositol were bound by Con A, and there were 4 binding sites each for mannose and myo-inositol. These results are consistent with reports that Con A is a tetramer comprised of 4 identical subunits and that each subunit has one saccharide binding site (Goldstein, I. J., Hollerman, C. E., and Smith, E. E. (1965) Biochemistry, Vol. 4, pages 876-883; Reeke, G. N., Jr., Becker, J. W., Cunningham, B. A., Bunther, G. R., Wang, J. L., and Edelman, G. M. (1974) Ann. N.Y. Acad. Sci., Vol. 234, pages 369-382; So, L. L., and Goldstein, I. J., (1986) Biochim. Biophys. Acta., Vol. 165, pages 398-404; Tanaka, I, Abe, Y., Hamada, T., Yonemitsu, O., and Ishii, S. (1981) J. Biochem., Vol. 89, pages 1643-1646).

In sum, Con A binds specifically to PI and this binding probably involves the inositol moiety of PI. This, therefore, represents a new, useful unobvious and generally unrecognized specificity for Con A.

TABLE 1

| Suppression of Con A activation of lymphocytes mitogenesis by α-MM or myo-inositol | | |
|---|---|---|
| INHIBITOR | DPM × 10⁻³ | % SUPPRESSION |
| None | 124 ± 10 | 0 |
| α-methyl mannoside | 1.3 ± 0.2 | 99 |
| myo-inositol | 86 ± 8 | 31 |

Cultures containing $2 \times 10^5$ mouse spleen lymphocytes in 0.2 ml medium were stimulated with 6 μg Con A/ml in the presence of 40 μmoles/ml of α-MM or myo-inositol and incubated for 48 hours. DNA synthesis was determined by pulsing the cultures 4 hours prior to harvesting with 1 μCi of [³H]-thymidine. The values represent the geometric mean of quadruplicate cultures ±1 S E.

We claim:

1. A method for the detection of a phosphatidylinositol within a sample comprising the steps of (a) contacting the sample with Concanavalin A and (b) detecting any phosphatidylinositol bound to the Concanavalin A.

* * * * *